(12) United States Patent
Leibovici

(10) Patent No.: US 11,458,245 B2
(45) Date of Patent: Oct. 4, 2022

(54) ACCESSORY HOLDER WITH SYRINGE ASSEMBLY REMOVAL TOOL

(71) Applicant: VAPOCOOLSHOT, INC., Wellington, FL (US)

(72) Inventor: Jacob Leibovici, Wellington, FL (US)

(73) Assignee: VAPOCOOLSHOT, INC., Boca Raton, FL (US)

( * ) Notice: Subject to any disclaimer, the term of this patent is extended or adjusted under 35 U.S.C. 154(b) by 304 days.

(21) Appl. No.: 16/573,736

(22) Filed: Sep. 17, 2019

(65) Prior Publication Data

US 2020/0093982 A1 Mar. 26, 2020

Related U.S. Application Data

(60) Provisional application No. 62/732,236, filed on Sep. 17, 2018.

(51) Int. Cl.
| | | |
|---|---|---|
| *A61M 5/32* | (2006.01) | |
| *A61M 5/00* | (2006.01) | |
| *B01L 9/00* | (2006.01) | |
| *A61B 50/36* | (2016.01) | |

(52) U.S. Cl.
CPC ............ *A61M 5/008* (2013.01); *A61B 50/362* (2016.02); *A61M 5/3205* (2013.01); *B01L 9/00* (2013.01); *A61M 2209/08* (2013.01)

(58) Field of Classification Search
CPC ...... A61M 5/008; A61M 5/3205; A61M 5/50; A61M 2209/08; A61B 50/362; B01L 9/00; B01L 9/06; B01L 2200/023; B01L 2200/082; B01L 2300/0829
USPC ........ 206/363–366, 369, 370, 477, 481–483; 211/85.13
See application file for complete search history.

(56) References Cited

U.S. PATENT DOCUMENTS

| | | | | |
|---|---|---|---|---|
| 4,863,451 | A * | 9/1989 | Marder | A61M 5/008 604/403 |
| 5,190,169 | A * | 3/1993 | Sincock | A61M 5/3213 206/366 |
| 5,823,363 | A * | 10/1998 | Cassel | A61M 5/3213 211/60.1 |
| 8,342,841 | B2 * | 1/2013 | Vogel | A61C 19/02 433/77 |
| 10,507,072 | B1 * | 12/2019 | Misle | A61B 50/22 |
| 2015/0094661 | A1 * | 4/2015 | Leibovici | A61M 5/3137 604/112 |

* cited by examiner

*Primary Examiner* — Luan K Bui
(74) *Attorney, Agent, or Firm* — McHale & Slavin, P.A.

(57) ABSTRACT

A medical procedure accessory components holding unit and methods of using thereof. The accessory holder is designed to hold and store one or more components or medical devices that could be used in a medical procedure, particularly medical devices, for applying an anesthetic. The accessory holder may include four (4) medical device storage or use modules: a syringe disposal device module, a dispensing tool module, a canister module, and a syringe attachment module.

12 Claims, 31 Drawing Sheets

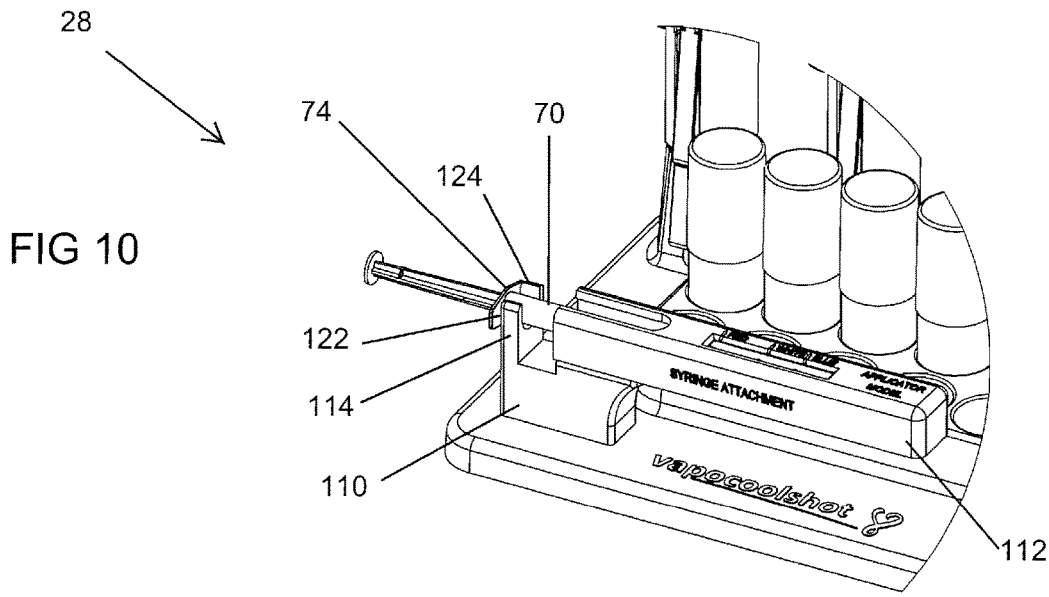
FIG 10
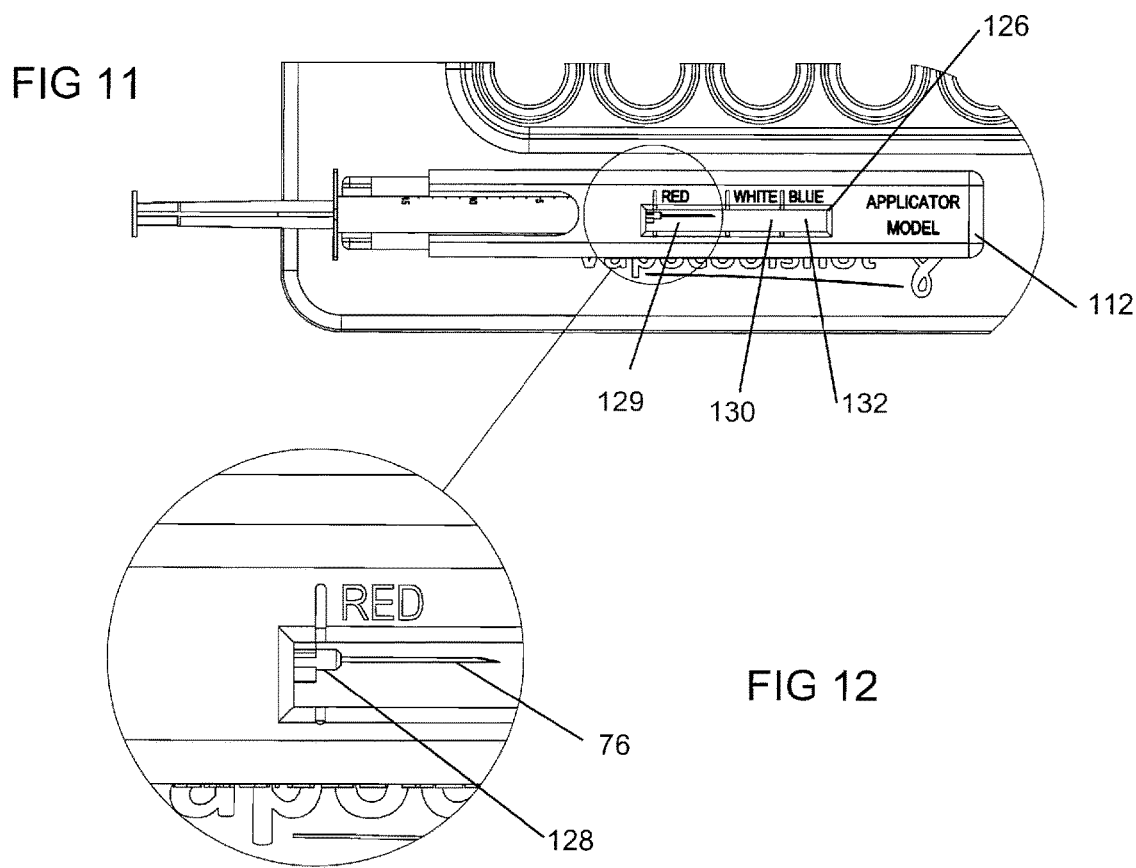
FIG 11
FIG 12

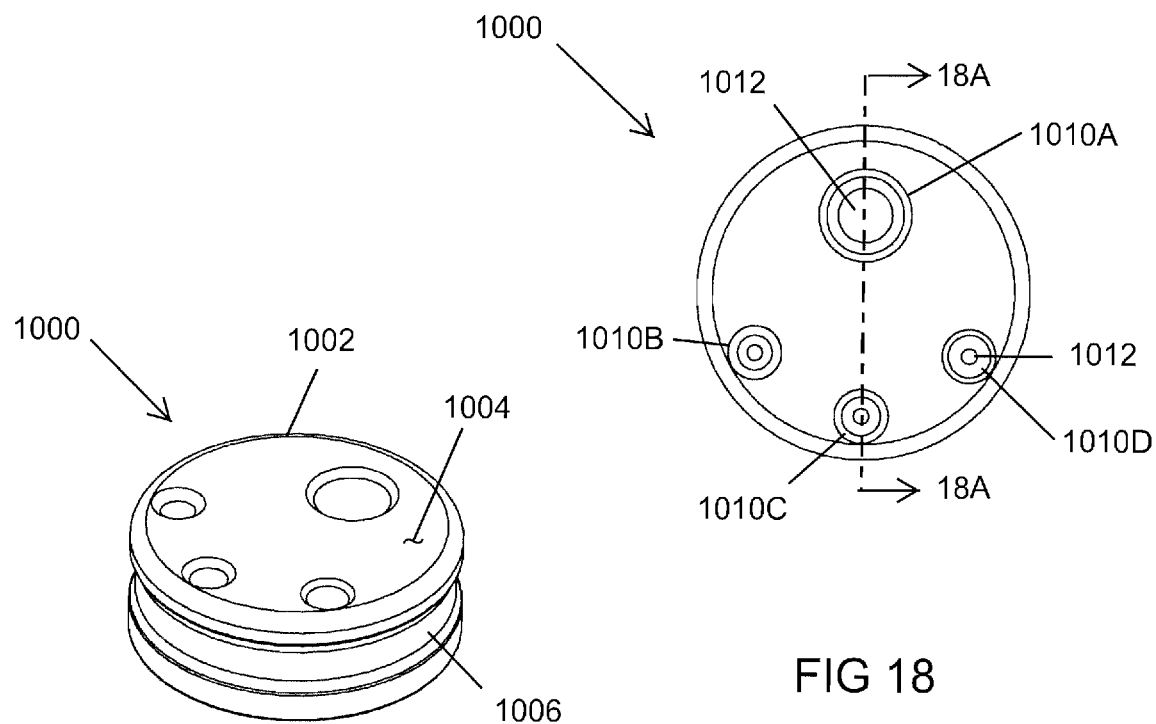

ACCESSORY HOLDER WITH SYRINGE ASSEMBLY REMOVAL TOOL

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 62/732,236 entitled "ACCESSORY HOLDER WITH SYRINGE ASSEMBLY REMOVAL TOOL", filed Sep. 17, 2108. The contents of the above referenced application are incorporated herein by reference.

FIELD OF THE INVENTION

The present invention relates to methods and apparatus for application of an anesthetic to a patient; more particularly, to methods and apparatus for use in a medical procedure, and includes a medical procedure accessory components holding unit for procedures requiring dispensing an endothermic gas from an applicator or dispensing tool.

BACKGROUND OF THE INVENTION

Syringes are employed millions of times daily all over the world to inject medicines into people as well as animals. Many times, injections are made in areas of the body that are somewhat less sensitive to pain. Other locations of the body where injections are contemplated are significantly more sensitive to pain, and the patient feels a pinching sensation that may be quite painful as the syringe needle is inserted beneath the skin. Such areas include, for example, gums, areas of the face such as the forehead, as well as the lips. To minimize the pain that results when the injection needle penetrates, for example, a patient's gums, the dental practitioner will often apply a topical agent to the injection site using a cotton swab. Because the deadening agent is only applied topically, it is not effective, as it does not cross the skin/mucosal membranes and misleads the patient into a false expectation of a painless injection. As a result, injecting an anesthetic often causes significant pain at the injection site. In other cases, such as diabetics, patients may be required to self-medicate on a daily basis. The repeated injections often create sensitive areas where injections are painful to the patient. This pain may cause patients to delay or omit medication to avoid the pain associated therewith.

SUMMARY OF THE INVENTION

The present invention relates to a medical procedure accessory components holding unit, and methods of using thereof. The accessory holder is designed to hold and store one or more components or medical devices that could be used in a medical procedure, particularly medical devices, for applying an anesthetic. The accessory holder may include four (4) medical device storage or use modules: a syringe disposal device module, a dispensing tool module, a canister module, and a syringe attachment module.

Accordingly, it is an objective of the invention to provide methods and apparatus relating to application of an anesthetic to a patient.

It is a further objective of the invention to provide an apparatus, and associated methods of use, which includes a medical procedure accessory components holding unit.

It is yet another objective of the invention to provide methods and apparatus for use in a medical procedure which includes a medical procedure accessory components holding unit for procedures requiring dispensing an endothermic gas from an applicator or dispensing tool.

It is a still further objective of the invention to provide an accessory holder having a syringe disposal device module.

It is a further objective of the invention to provide an accessory holder having a dispensing tool module.

It is yet another objective of the invention to provide an accessory holder having a canister module.

It is a still further objective of the invention to provide an accessory holder having a syringe attachment module.

It is a further objective of the invention to provide an accessory holder having a syringe disposal device module, a dispensing tool module, a canister module, and a syringe attachment module.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 10 is a close-up view of the syringe attachment module;

FIG. 11 illustrates a viewing window of the syringe attachment module;

FIG. 12 is a close-up view of the viewing window;

FIG. 17 is a perspective view of an alternative embodiment of an accessory holder unit, FIG. 18 is a top view of the accessory holder unit illustrated in FIG. 17;

DETAILED DESCRIPTION OF THE INVENTION

Figure 1:
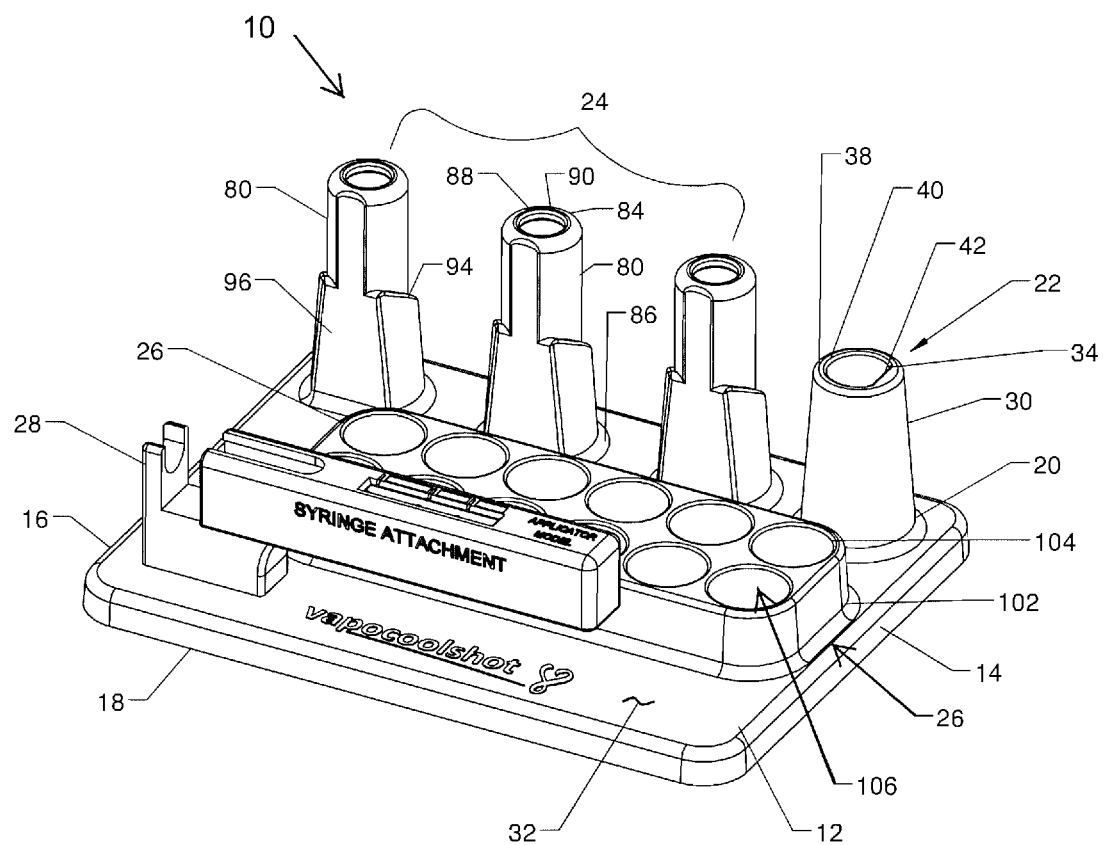
FIG. 1 is a perspective view of an illustrative embodiment of an accessory holder unit.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Figure 2:
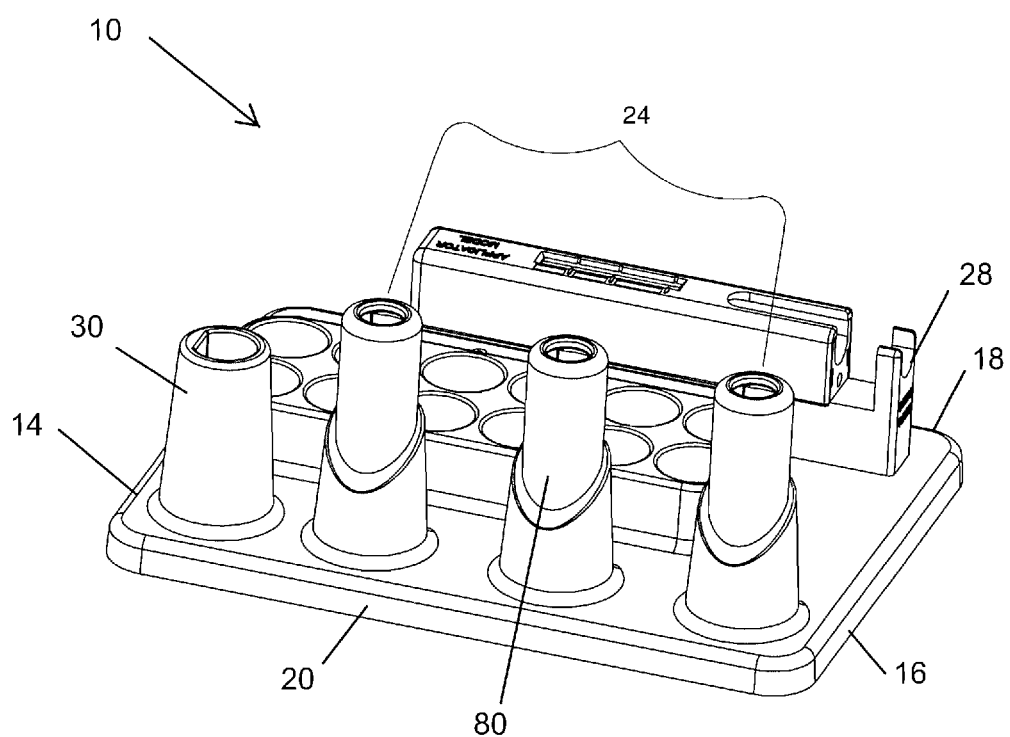
FIG. 2 is an alternative perspective view of the accessory holder unit.

Referring to FIGS. 1 and 2, an illustrative example of a medical procedure accessory components holding unit, referred to generally as an accessory holder 10, is shown. The accessory holder 10 is designed to hold and store one or more components or medical devices that could be used in a medical procedure, particularly medical devices, and methods of use thereof, for applying an anesthetic. The accessory holder 10 comprises a support panel 12 having two opposing side walls 14 and 16, a front wall 18, and an opposing back wall 20. The two opposing side walls 14 and 16 are shown arranged in a generally parallel manner relative to each other. The front wall 18 and the opposing back wall 20 are shown arranged in a generally parallel manner relative to each other. The support panel 12 provides one or more medical device storage or use modules. The medical device storage or use modules are designed and configured to store a component that may be used in a medical procedure or aid in its use. Referring to FIG. 1, the accessory holder 10 is shown having four (4) medical device storage or use modules: a syringe disposal device module 22, a dispensing tool module 24, a canister module 26, and a syringe attachment module 28.

Figure 3:
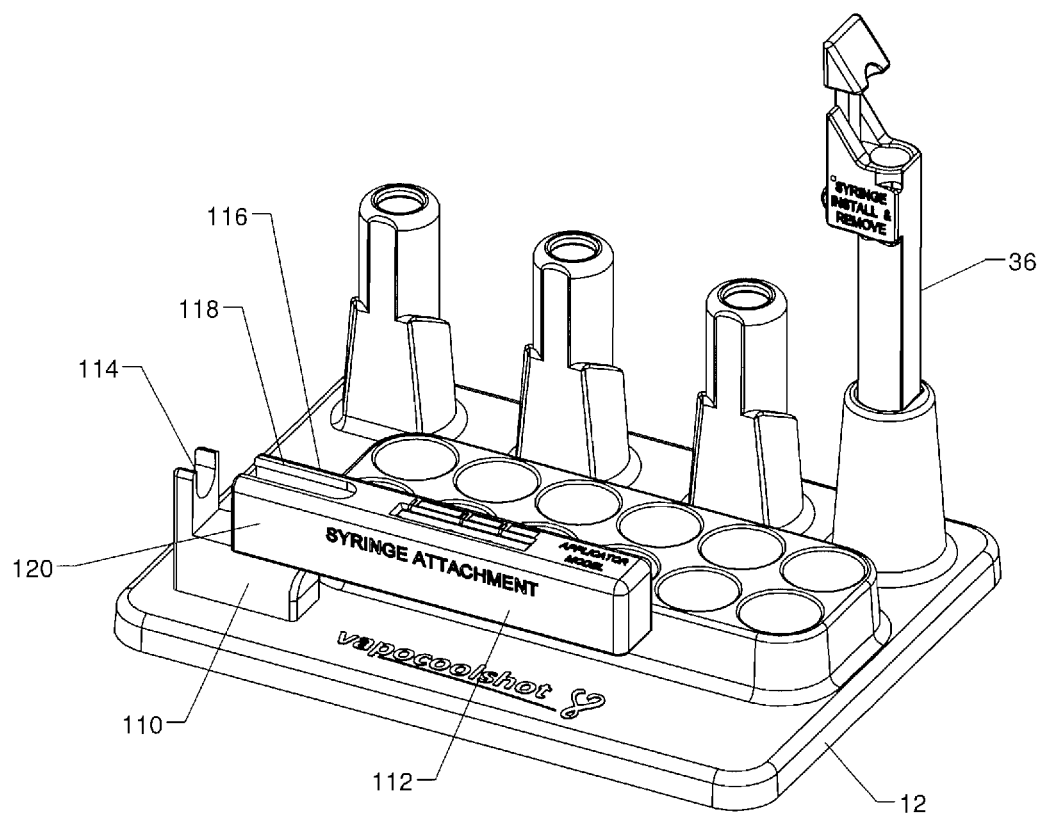
FIG. 3 is a perspective view of the accessory holder unit shown with a syringe disposal device.

The accessory holder 10 is shown having a single syringe disposal device module 22. However, additional syringe disposal device modules 22 may be included. The syringe disposal device module 22 is shown having a syringe disposal device module main body or post 30. The syringe disposal device module main body or post 30 is shown having a generally tubular body shape extending upwardly, i.e. away from the support panel surface 32. The syringe disposal device module main body 30 comprises an opening 34 sized and shaped to receive and hold a syringe disposal device 36, see FIG. 3, therein. The internal portion of the syringe disposal device module main body 30 is preferably designed to mirror the shape or configuration of the syringe disposal device 36 in order to securely maintain the syringe disposal device 36 within.

Figure 4:
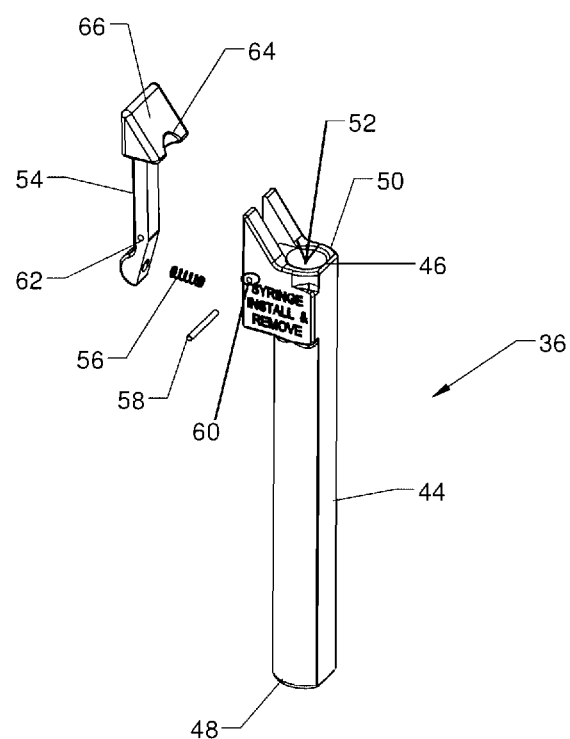
FIG. 4 is an exploded view of an illustrative example of the syringe disposal device.
Figures 5, 6:
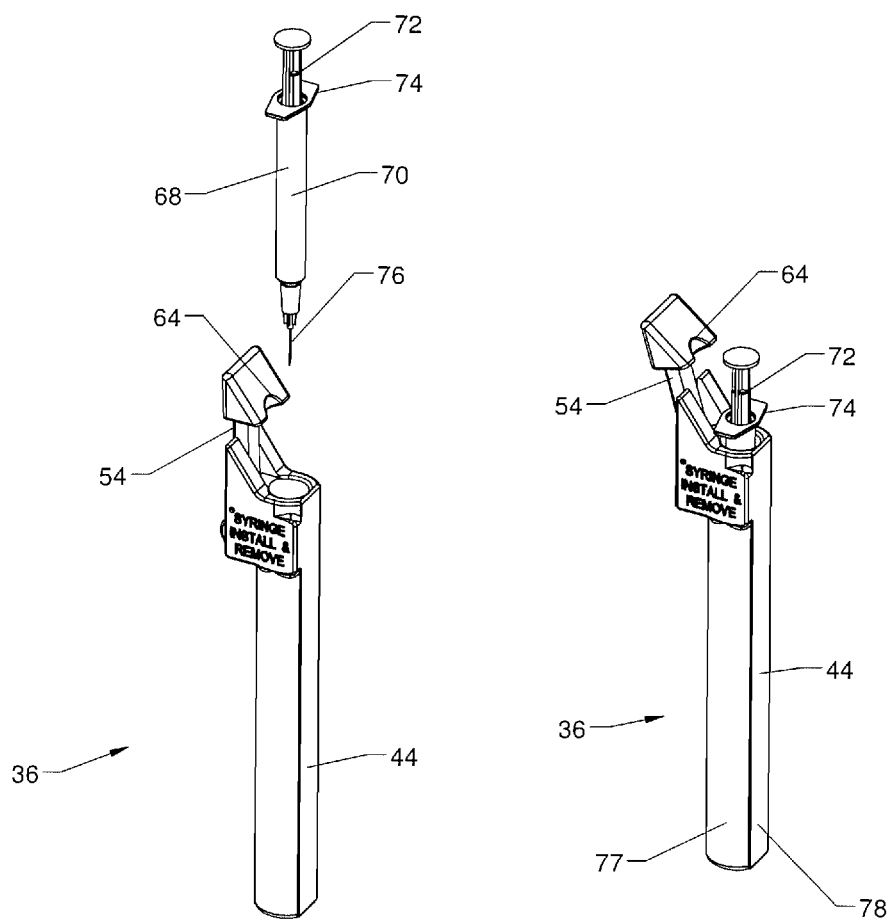
FIG. 5 illustrates the syringe disposal device prior to insertion of a syringe with needle.
FIG. 6 illustrates the syringe disposal device with the syringe with needle inserted therein.

For example, the syringe disposal device module main body 30 may contain an outer perimeter 38 that assumes a generally tubular shape, and an inner perimeter that includes a semicircle shape 40 and a linear shape 42. Such configuration mirrors the shape of the syringe disposal device 36 shown in FIG. 3 and FIG. 4. The syringe disposal device 36 is shown having an elongated main body 44 having a top end 46 and a closed bottom end 48. The top end 46 comprises an opening 50, exposing an internal passageway 52. A latch 54, with spring 56, is attached to a portion of the main body 44 via a pin 58 at main body opening 60 and latch opening 62. The latch 54 comprises a semi-circular cut out portion 64 from an angled surface 66 which may engage at least a portion of a syringe 68, see FIG. 5, when the syringe is inserted into the internal passageway 52.

In use, as a syringe 68 is inserted therein, the syringe barrel 70 may push against the semi-circular cut out portion 64 and move the latch 54. Once the syringe is fully inserted, the latch 54 may move back, with the semi-circular cut out portion 64 resting against at least a portion of a syringe plunger 72 or barrel flange 74. This locks the syringe 68 in place with the needle 76 resting inside the main body 44, thus reducing the risk of direct contact with the needle during the disposal process. The main body 44 may have a shape that mirrors the shape of the internal portion of the disposal device module main body 30, having a circular or semi-circular portion 77 and a planar or linear surface 78, see FIG. 6.

Figure 7:
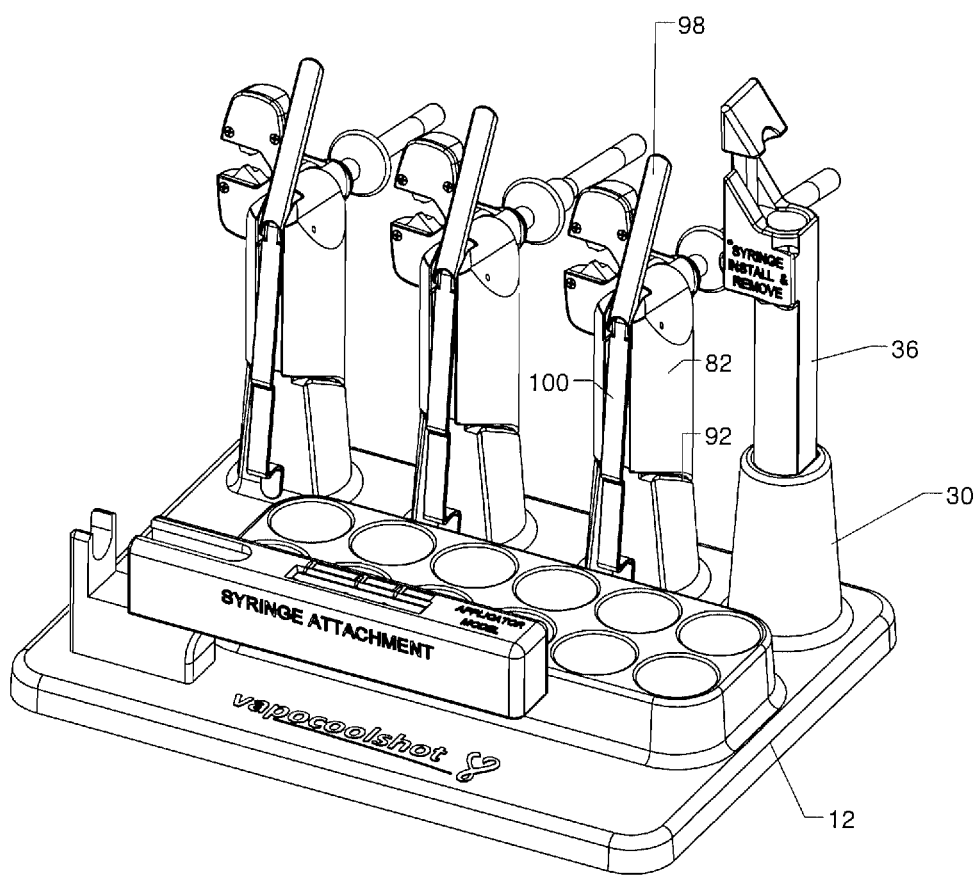
FIG. 7 is a perspective view of the accessory holder unit shown with a syringe disposal device and dispensing tools.

Referring back to FIG. 1 or FIG. 2, the dispensing tool module 24 is shown having multiple, three (3), modules. The dispensing tool module 24 comprises a dispensing tool module receiving body 80, configured to receive and hold a medical procedure dispensing tool such as those described in U.S. patent application Ser. No. 16/017,379, entitled "Method and Apparatus for Applying an anesthetic and Bactericide", filed on Jun. 25, 2018, the contents of which are herein incorporated by reference. While any of the dispensing tools described in the application may be used, the dispensing tool module receiving body 80 is described to fit and secure with the applicator as identified in application Ser. No. 16/017,379, with identifier number 200 as described in FIGS. 21-44. This applicator is identified as 82, see FIG. 7, in the current application. The dispensing tool module receiving body 80 comprises a first end 84, and a second, closed end 86, and extends upwardly from surface 32. The first end 84 comprises an opening 88, exposing an interior portion 90. At least a portion of the lower edges or surface 92 of the applicator 82, which may contain a canister (described below) therein, rests against ledge or shoulder 94 of the dispensing tool module receiving body 80. If the applicator 82 contains a canister therein, the canister rests within the interior portion 90. The dispensing tool module receiving body 80 may contain a planar or flat back surface 96, which may be configured to receive other components of the applicator 82, such as a trigger 98 or canister lift lever 100, see FIG. 7.

Figure 8:
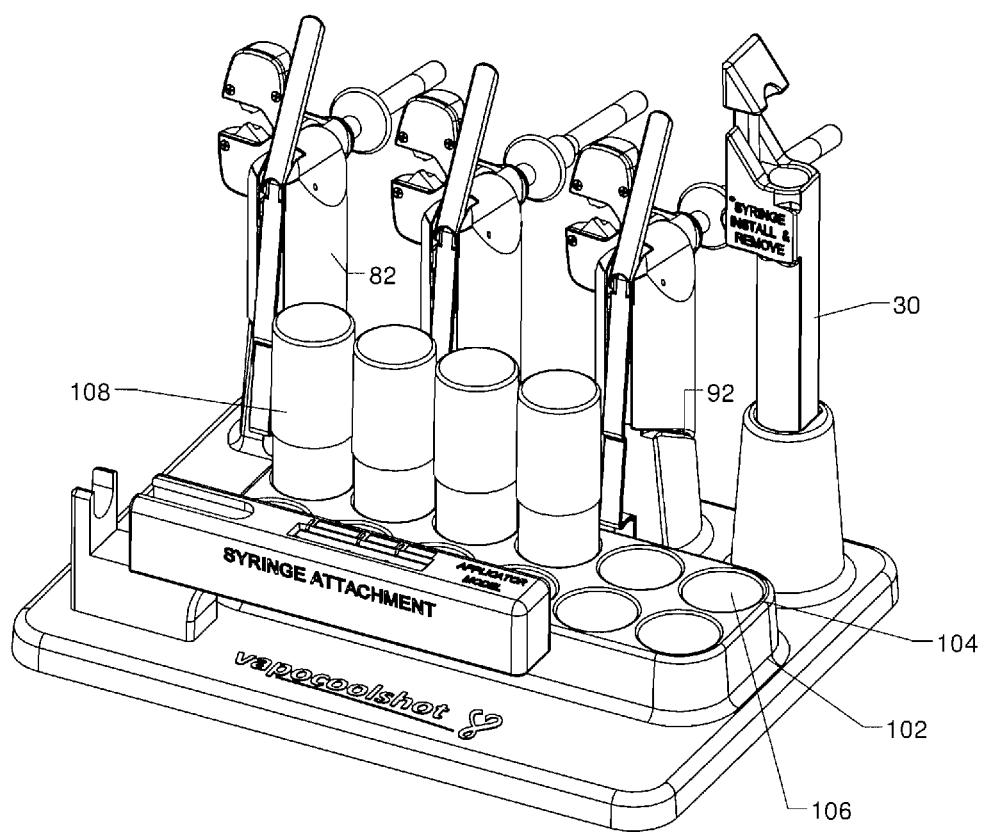
FIG. 8 is a perspective view of the accessory holder unit shown with a syringe disposal device, dispensing tools, and canisters.

Referring back to FIG. 1 or FIG. 2, the canister module 26 is shown as a raised platform 102 having one or more openings 104 and corresponding internal compartments 106 sized and shaped to received and store therein canister(s) 108, see FIG. 8. Canisters 108 preferably contain a medical agent, a composition, chemical, or compound to be used in a medical procedure. Such medical agent may be a gaseous (vapor) anesthetizing composition. Other medicines, such as BOTOX can be dispersed from other instruments, such as for example a syringe.

Figure 15:
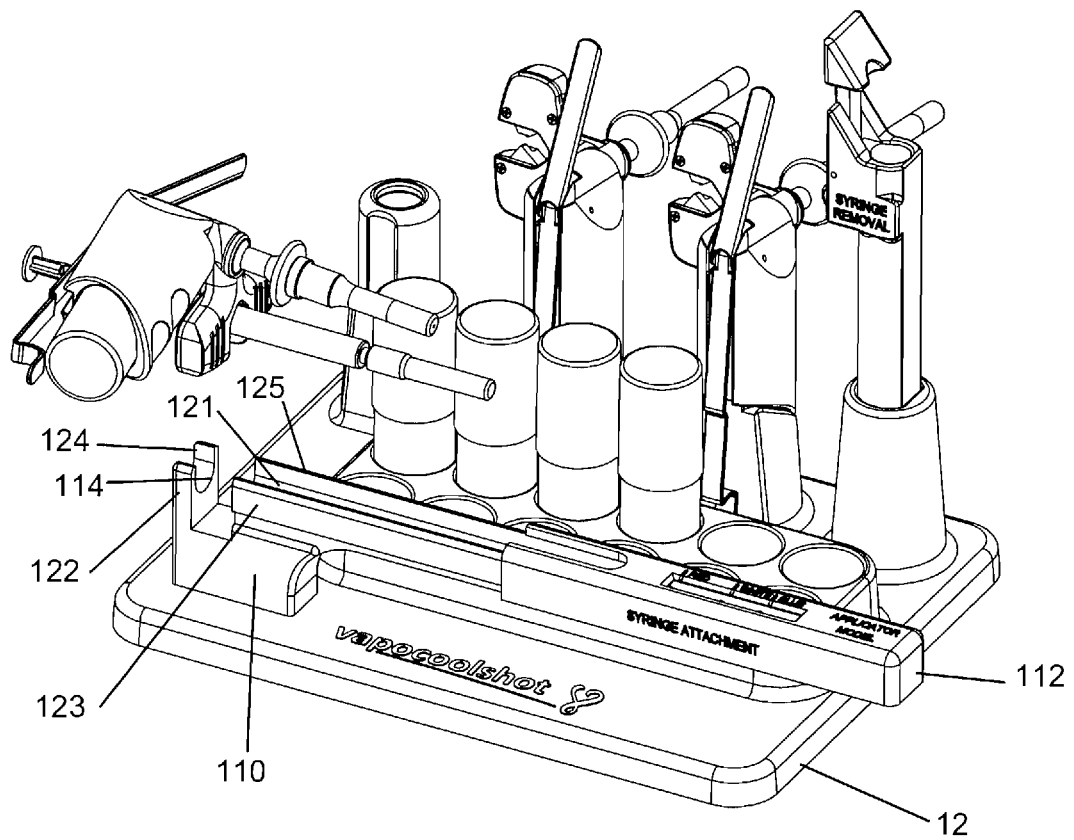
FIG. 15 illustrates the removal of the applicator device from the syringe attachment module.

The syringe attachment module 28 is configured to allow a user to safely load a syringe 68 and attach the syringe 68 to a dispensing device, such as the applicator 82. As shown in FIG. 10, the syringe attachment module 28 comprises a syringe attachment block 110 and a syringe attachment block safety cover 112. The syringe attachment block 110 comprises a syringe receiving area, illustrated as a cut out region 114 having a U-shaped outline. The syringe attachment block safety cover 112 is illustrated having a top surface 116 and two side surfaces 118 and 120, see FIG. 3. The syringe attachment block safety cover 112 may include a ridge or guide (not shown) that slidable engages with a channel or track 121 via channel or track walls 123 and 125, see FIG. 15, thus allowing the syringe attachment block safety cover 112 to move in two directions.

Figure 9:
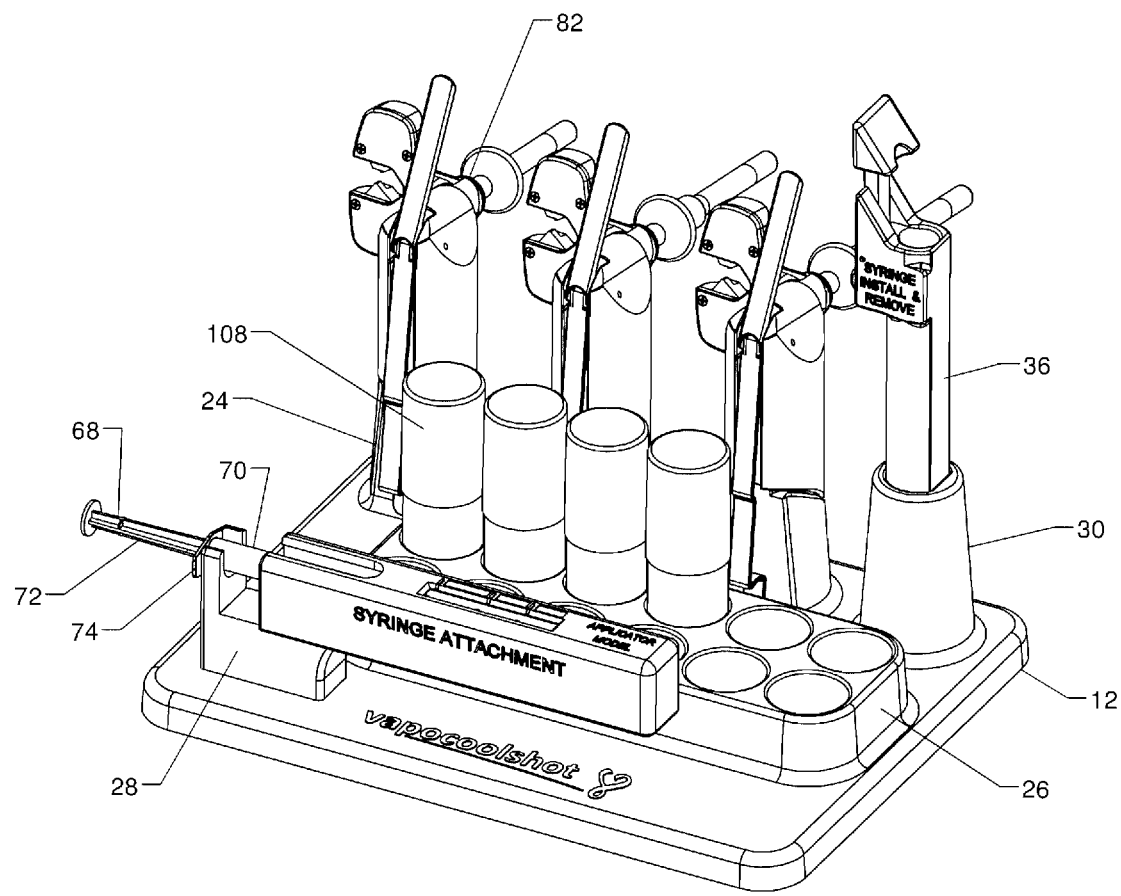
FIG. 9 is a perspective view of the accessory holder unit shown with a syringe disposal device, dispensing tools, canisters, and a syringe.
Figure 13:
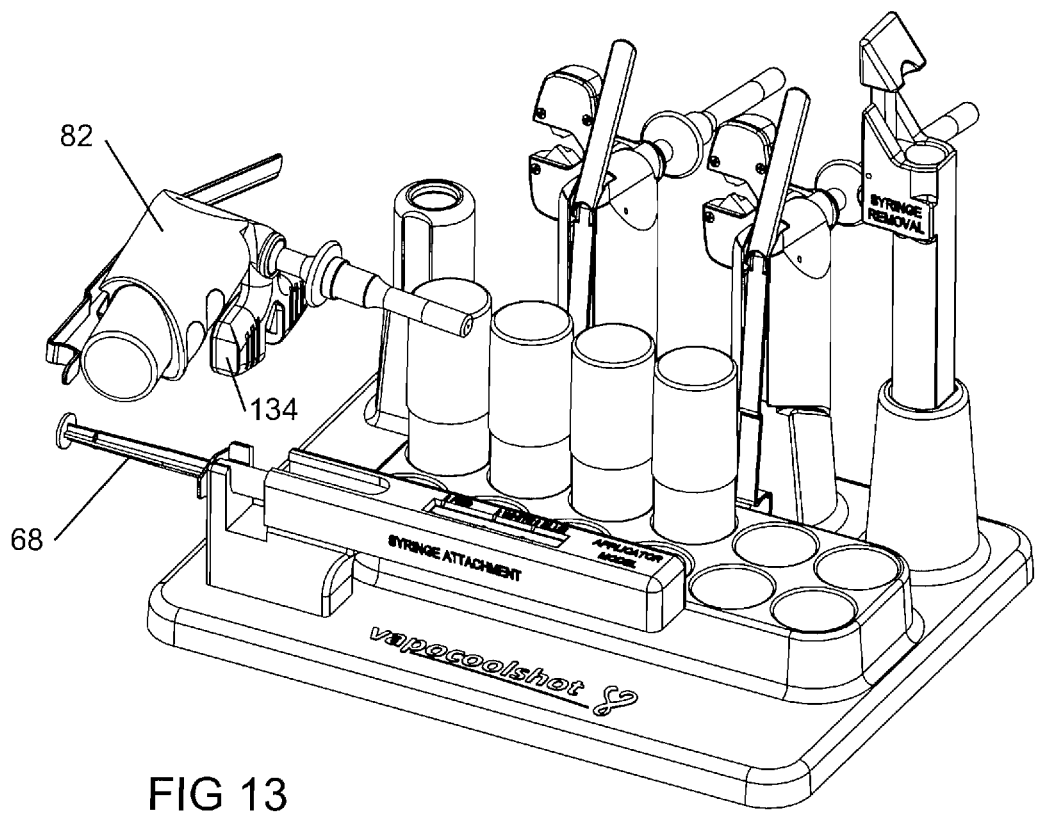
FIG. 13 illustrates the accessory holder unit prior to the applicator device engaging with the syringe attachment module.
Figure 14:
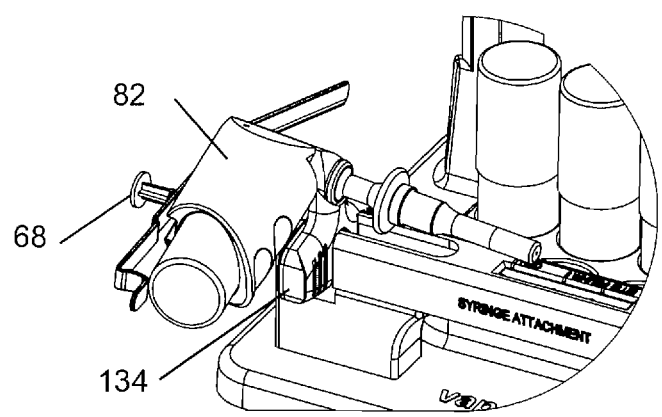
FIG. 14 illustrates engagement of the applicator device and the syringe attachment module.

In use, the syringe 68 is placed in the syringe attachment block 110 so that the syringe barrel 70 rests within the syringe receiving area U-shaped cut out region 114, see FIG. 9 and FIG. 10, with the syringe flange 74 resting against arms 122 and 124 of the syringe receiving area U-shaped cut out region 114. The syringe attachment block safety cover 112 contains a viewing window 126, see FIG. 11, that lets the user determine which applicator 82 should be used. The type of applicator 82 used depends on the hub 128 of the needle 76, see FIG. 12. As shown by the viewing window 126, three different applicators may be used, a red section 129 indicating use of an applicator for small syringes that are 6 cm to 7 cm long, a white section 130 indicating use of an applicator for medium syringes, 7 cm to 8.5 cm, and a blue section 132, indicating use of an applicator for long syringes, 8.5 cm to 10 cm. Once the syringe attachment block safety cover 112 is moved into place, the user can position the applicator 82 over the syringe 68 so that a syringe barrel clamp 134 can engage with the syringe 68. Then, the user simply pushes the applicator 82 onto the syringe 68 to snap the syringe 68 in place, see FIG. 13 and FIG. 14. Once secure, the user can slide the syringe attachment block safety cover 112 away from the block 110 so the syringe 68 can be removed, see FIG. 15.

Figure 16:
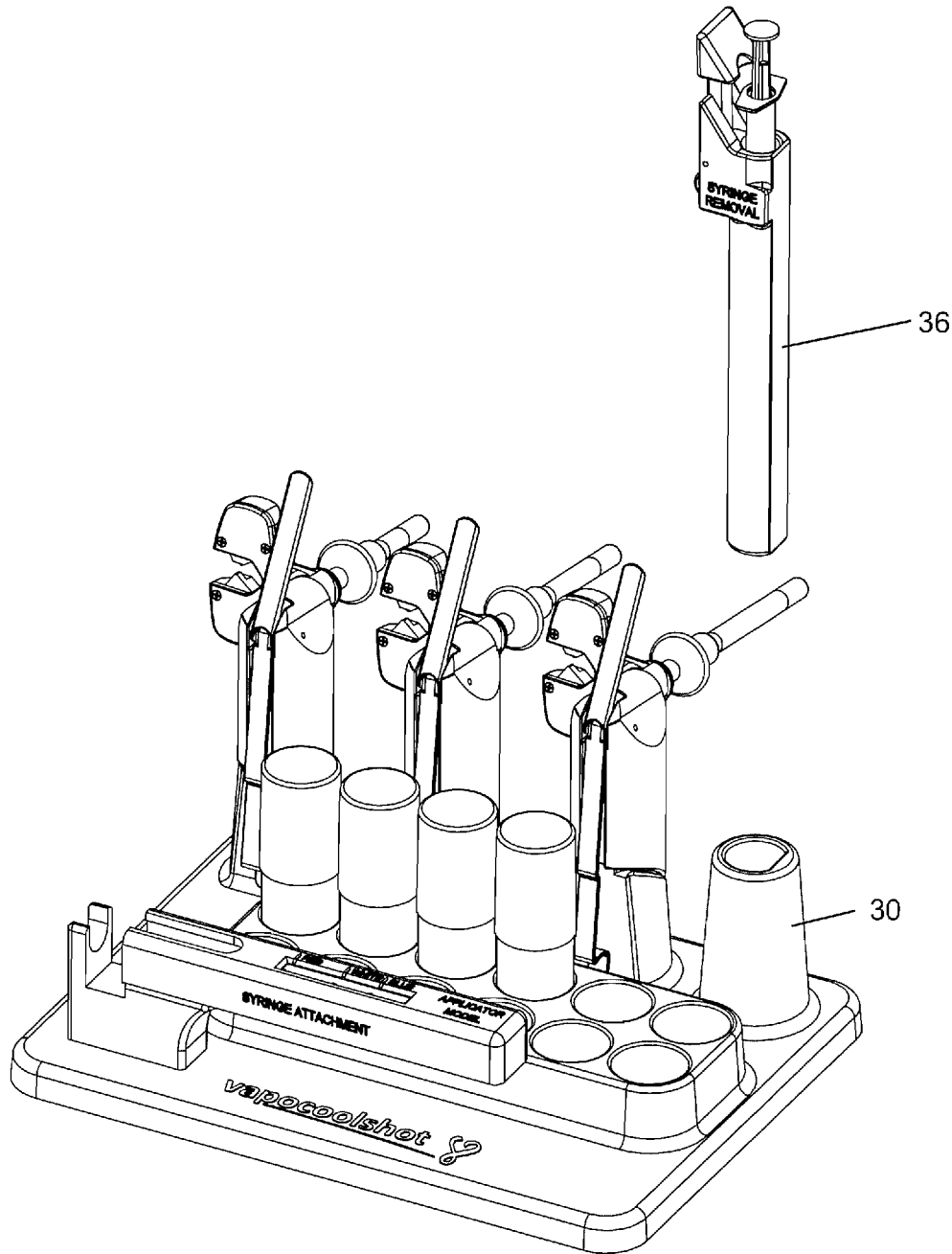
FIG. 16 illustrates a used syringe inserted within the syringe disposal device, shown removed from the accessory holder unit.
Figures 19, 20:
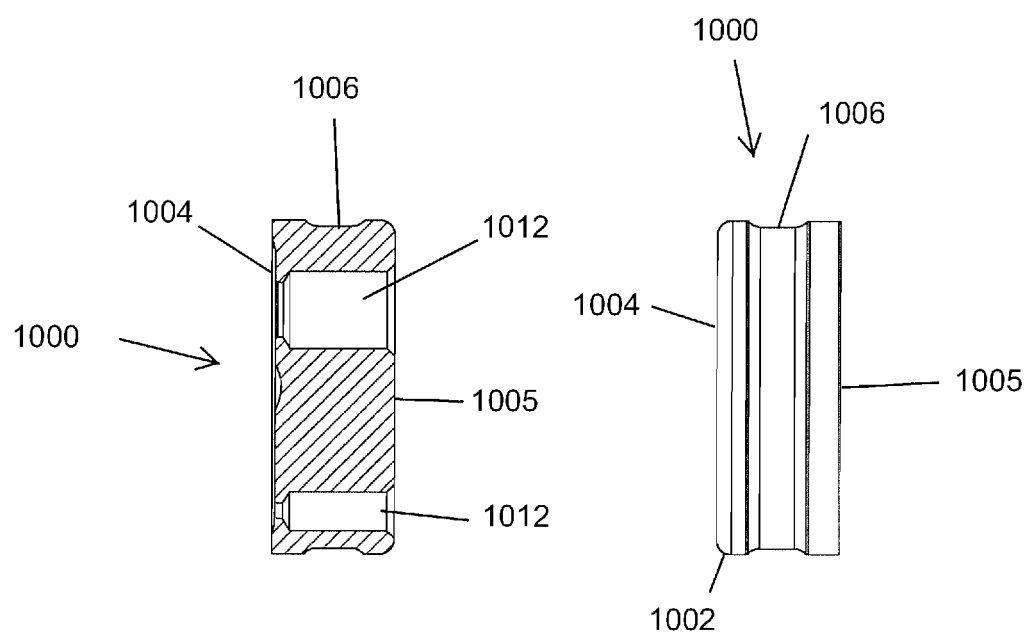
FIG. 19 is a side view of the accessory holder unit illustrated in FIG. 17.
FIG. 20 is a cross sectional view taken along lines 18A-18A in FIG. 18.

After the syringe is used in a medical procedure, the applicator 82, with the used syringe 68 attached to the syringe barrel clamp 134 can be inserted into the syringe disposal device 36 seated in the disposal device module main body 30 until the latch 54 locks the syringe 68 in place. The applicator 82 is twisted, thereby removing it from the syringe 68. The syringe disposal device 36 can then be removed from the disposal device module main body or post 30, see FIG. 16, and discarded properly in an approved sharps container.

FIGS. 17-20 illustrate an alternative embodiment of a medical procedure accessory components holding unit, referred to generally as an accessory holder 1000. The accessory holder 1000 is designed to hold and store one or more components or medical devices that could be used in a medical procedure, particularly medical devices, and methods of use thereof, for applying an anesthetic. The accessory holder 1000 comprises a base support structure 1002 having an upper surface 1004, a lower surface 1005, and a side wall 1006 separating the upper surface 1004 and the lower surface 1005. A plurality of openings 1010, referred to individually as 1010A-1010D, and corresponding internal compartments 1012 sized and shaped to received and store therein one or more components or medical devices that could be used in a medical procedure.

Figures 21, 22A:
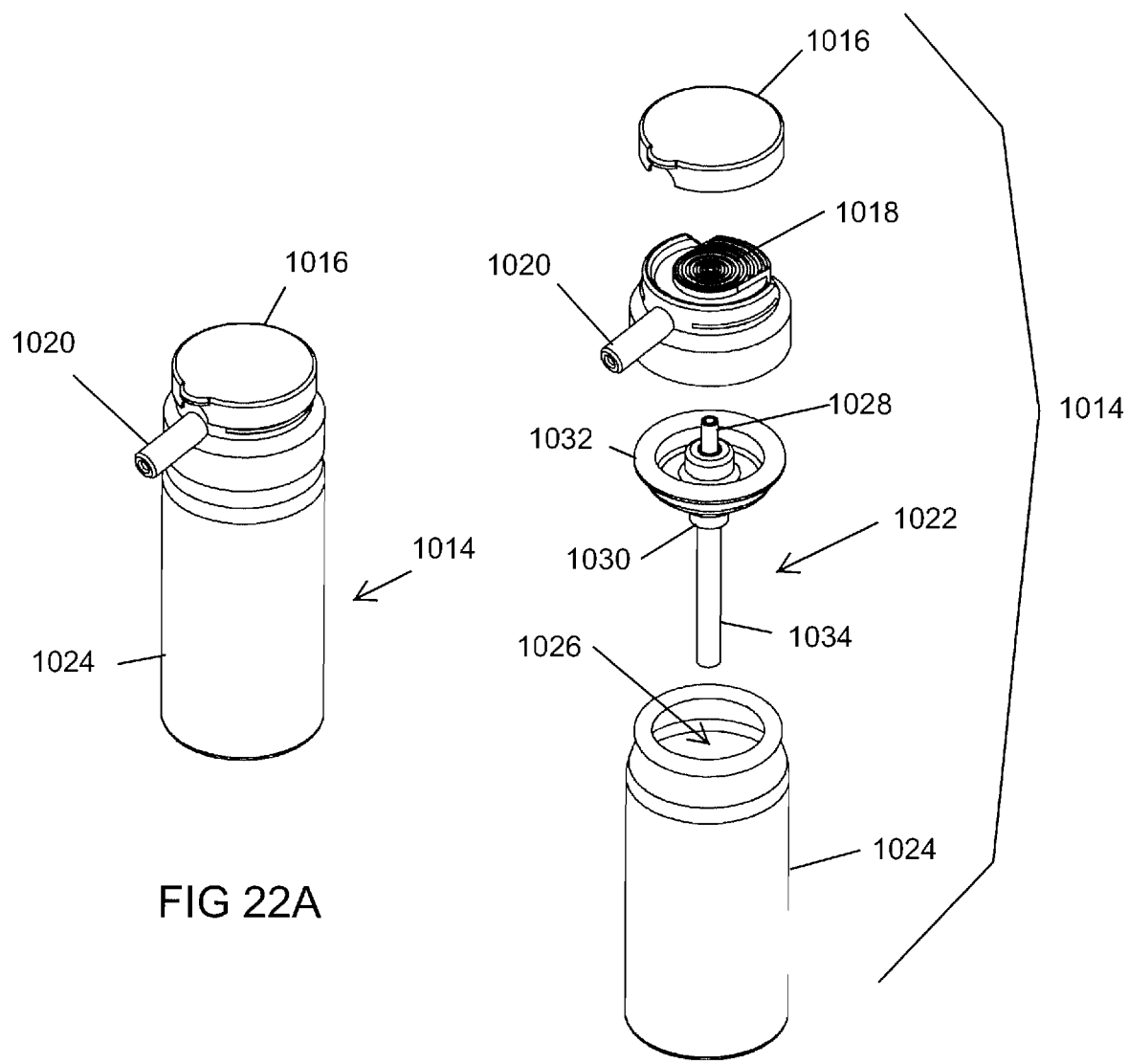
FIG. 21 is a perspective view of a canister.
FIG. 22A is an exploded view of the canister illustrated in FIG. 21.
Figure 22B:
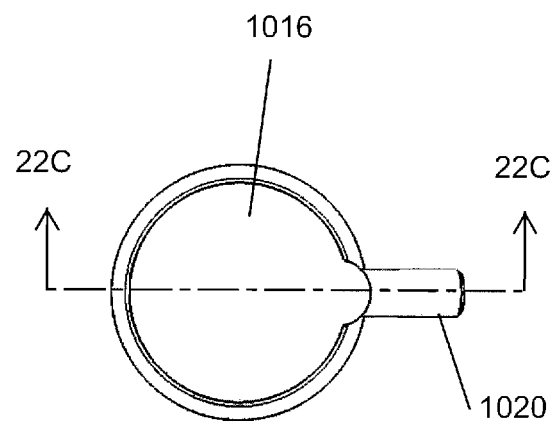
FIG. 22B is a top view of the canister cap, canister spout, and canister actuator.
Figure 22C:
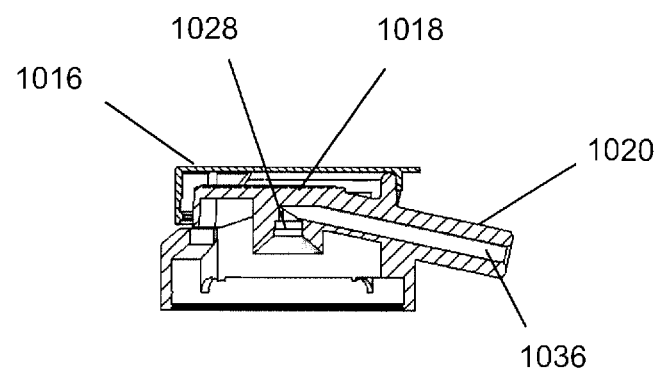
FIG. 22C is a partial cross sectional view taken along lines 22C-22C of FIG. 22B.

Referring to FIGS. 21-22C, an illustrative embodiment of a canister 1014 is shown. The canister 1014 functions in a similar manner as canister 108. Canister 1014 preferably contains a medical agent to be used in a medical procedure. Such medical agent may be a gaseous (vapor) anesthetizing composition. Canister 1014 comprises a cap 1016, an actuator 1018 and a spout 1020 configured to dispense or disperse the anesthetizing composition, a valve 1022, and a canister body 1024 sized and shaped to store the anesthetizing composition within the interior 1026. The valve 1022 comprises a stem 1028, a housing 1030, a mounting cup 1032, and a dip tube 1034. As a user applies a force or presses on actuator 1018, a spout dispensing tube 1036, see FIG. 22C, is brought into contact with the valve 1022, forcing fluid stored within the canister body 1024 to be expelled and dispersed to a target area, such as skin.

Figure 23:
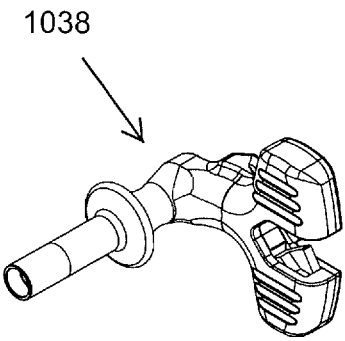
FIG. 23 is a perspective view of an alternative embodiment of a syringe holding nozzle.
Figure 24:
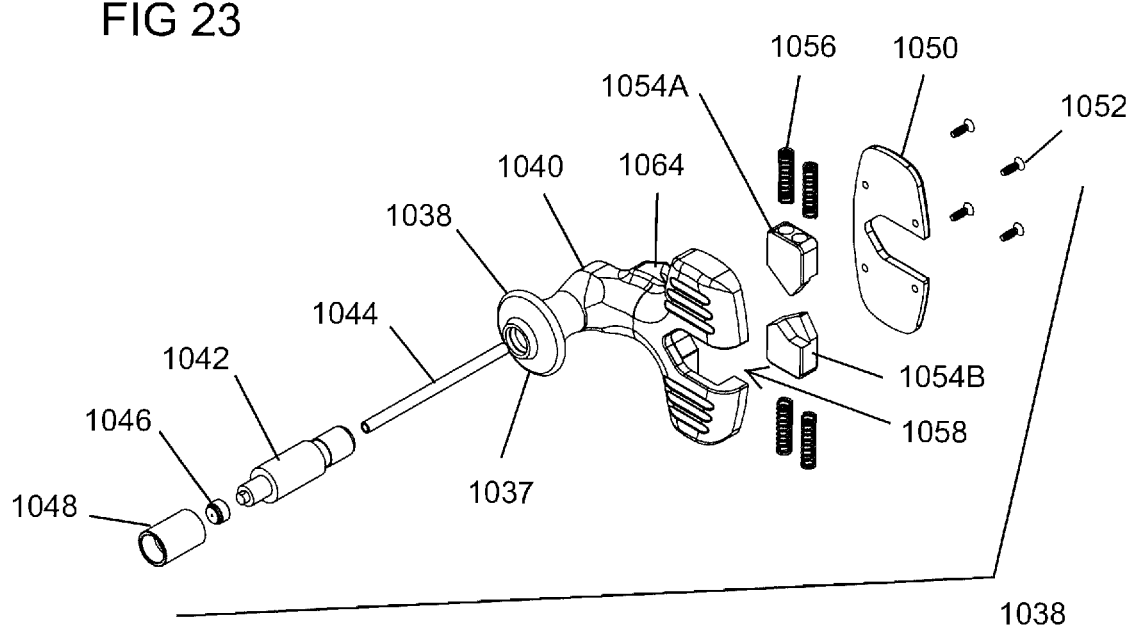
FIG. 24 is an exploded view of the syringe holding nozzle illustrated in FIG. 23.

FIGS. 23-24 illustrate a syringe holding nozzle 1038. The syringe holding nozzle 1038 functions in a similar manner as the syringe barrel clamp 134. The syringe holding nozzle 1038 comprises a clamp body 1040, a nozzle 1042, a nozzle tube 1044, a nozzle tip 1046, and a nozzle shroud 1048. A nozzle body cover 1050 secures to the nozzle clamp body 1040 via screws 1052. The nozzle clamp body 1040 houses clamps 1054A and 1054B. The clamps 1054A and 1054B may include springs 1056, allowing the clamps 1054A and 1054B to move inwardly when a force is applied, and move back to their resting position when the force is removed. The clamp body 1040 comprises a cut out section 1058 which is sized and shaped to receive a device, such as a barrel of a syringe.

Figure 25:
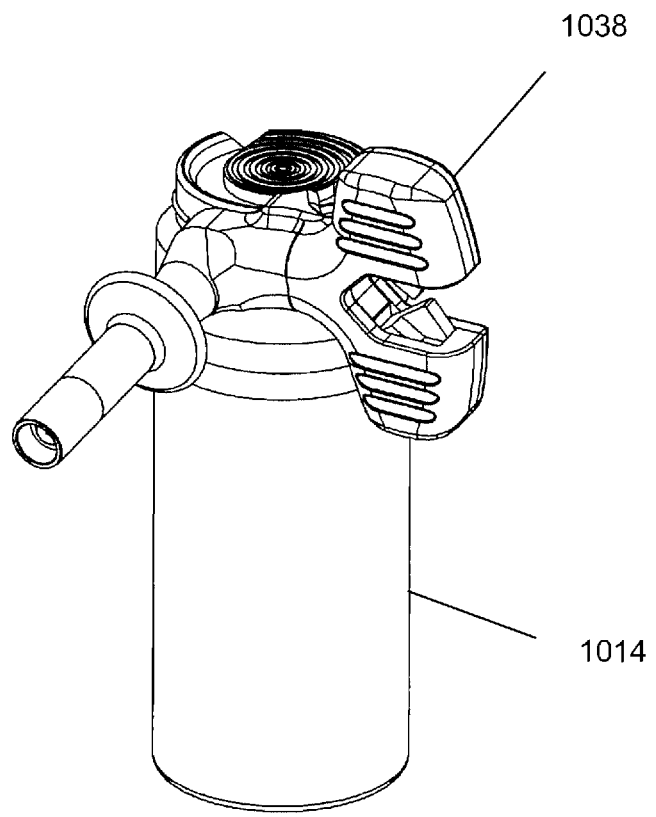
FIG. 25 illustrates the syringe holding nozzle illustrated in FIG. 23 secured to the canister illustrated in FIG. 21.
Figure 26A:
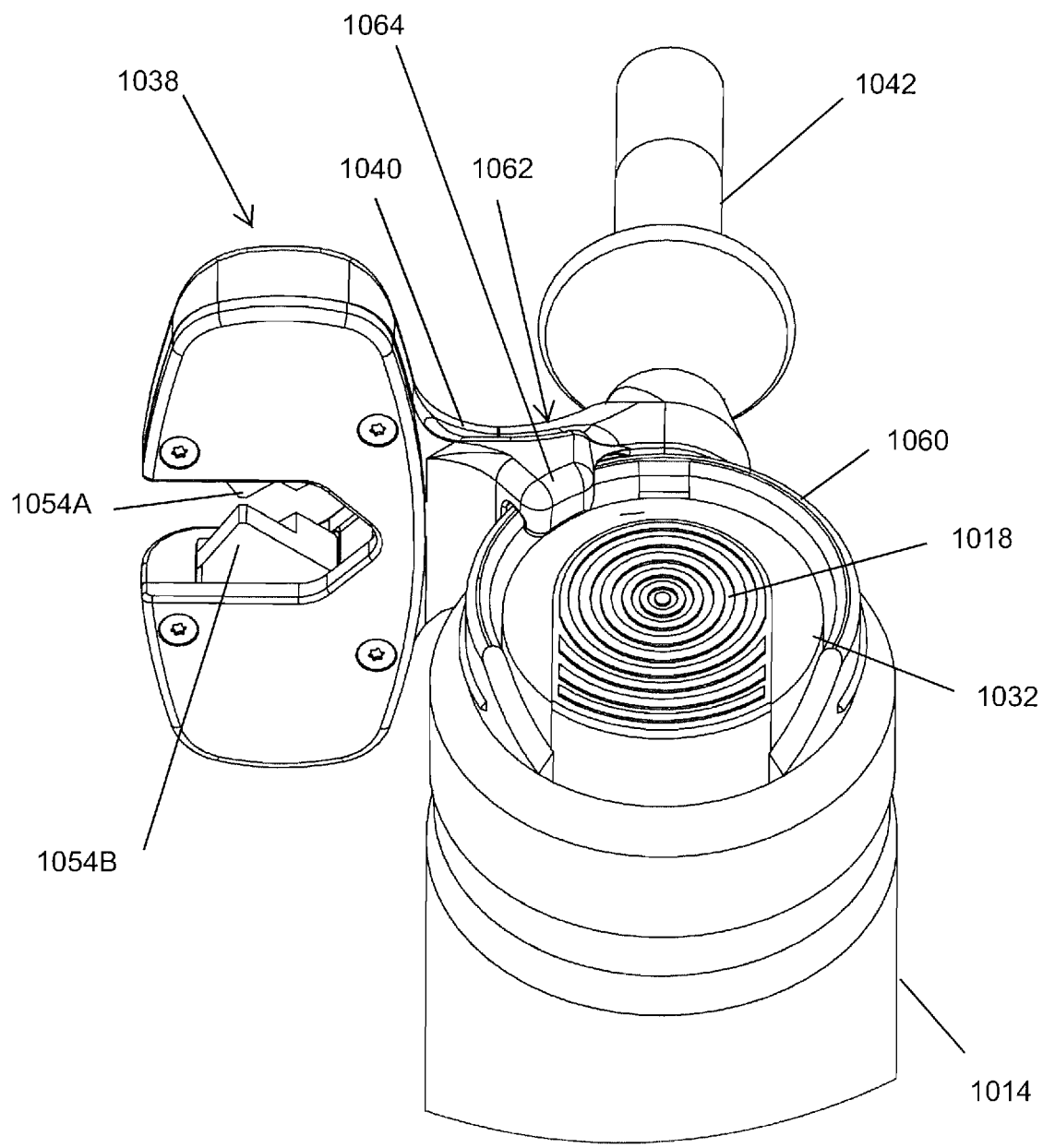
FIG. 26A shows the inside portion of the syringe holding nozzle as secured to the canister.
Figure 26B:
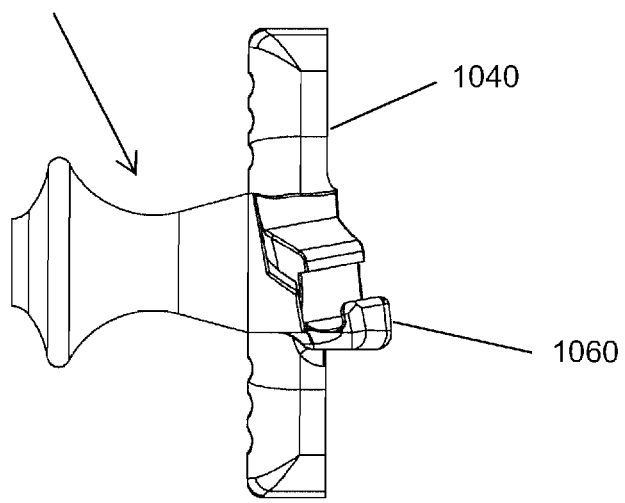
FIG. 26B is a top, partial view of the syringe holding nozzle.
Figure 26C:
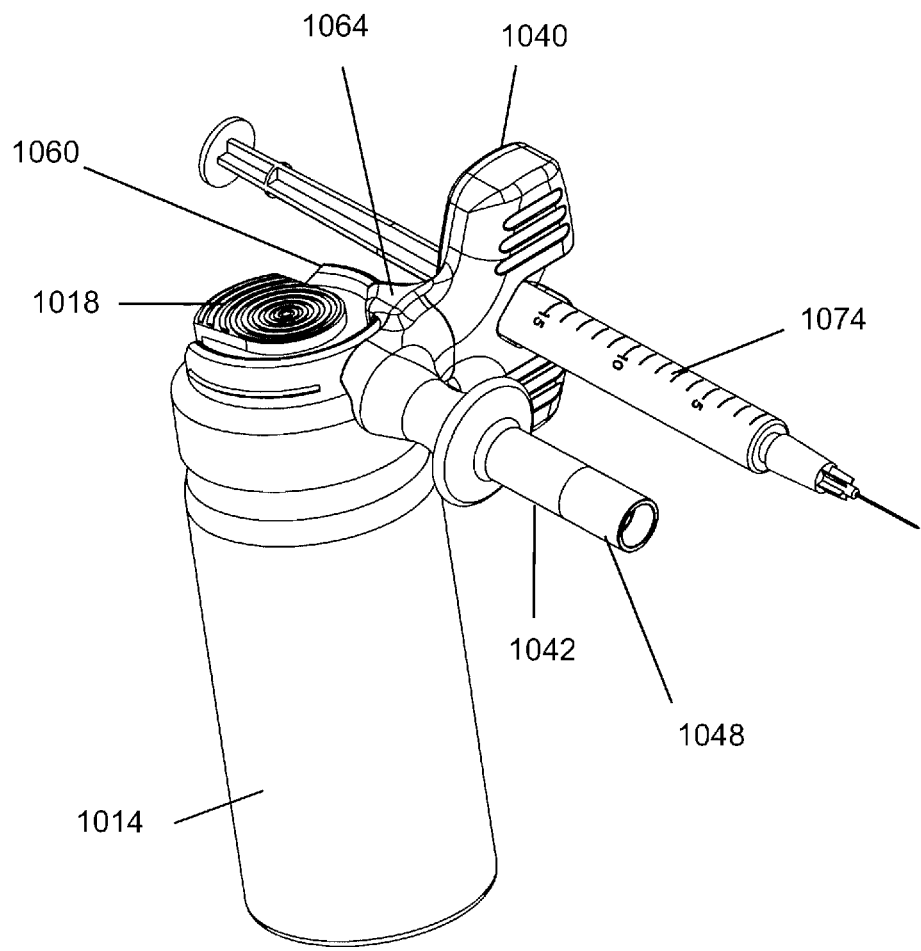
FIG. 26C is a top right perspective view of the canister with syringe holding nozzle, with a syringe attached thereto.
Figure 26D:
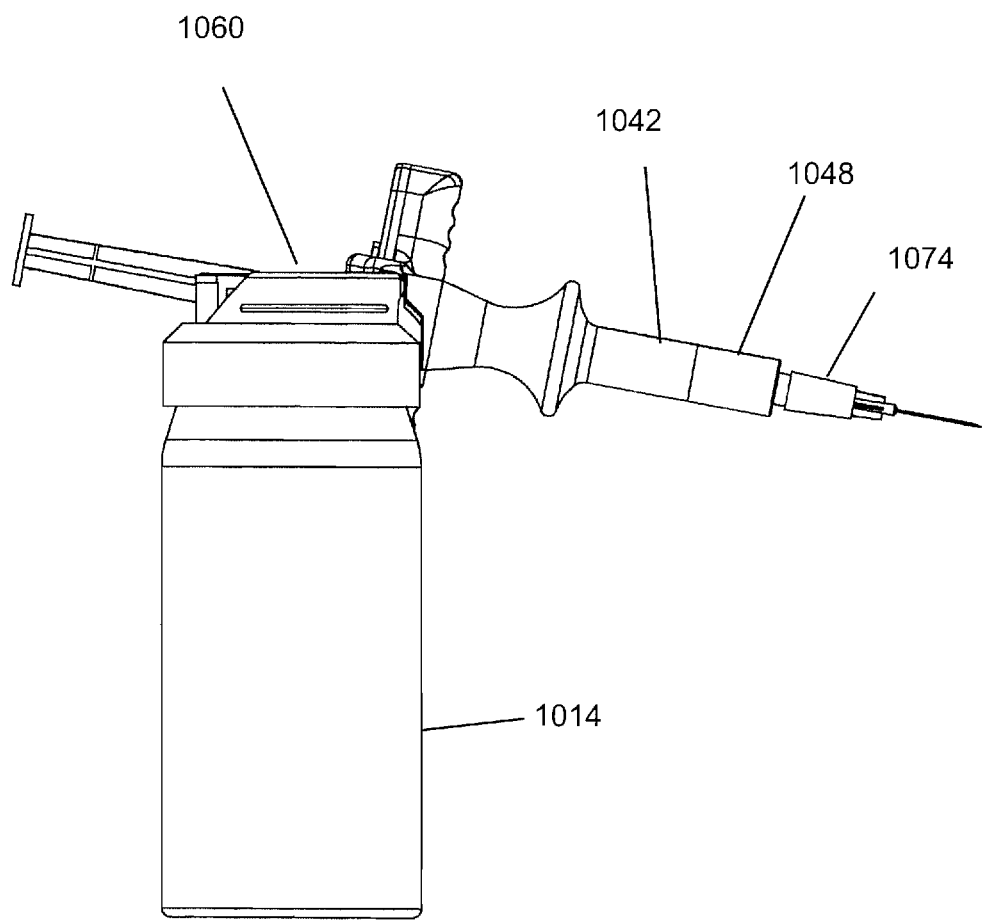
FIG. 26D is a right, side view of the canister with syringe holding nozzle, with a syringe attached thereto, shown in FIG. 26C.
Figure 26E:
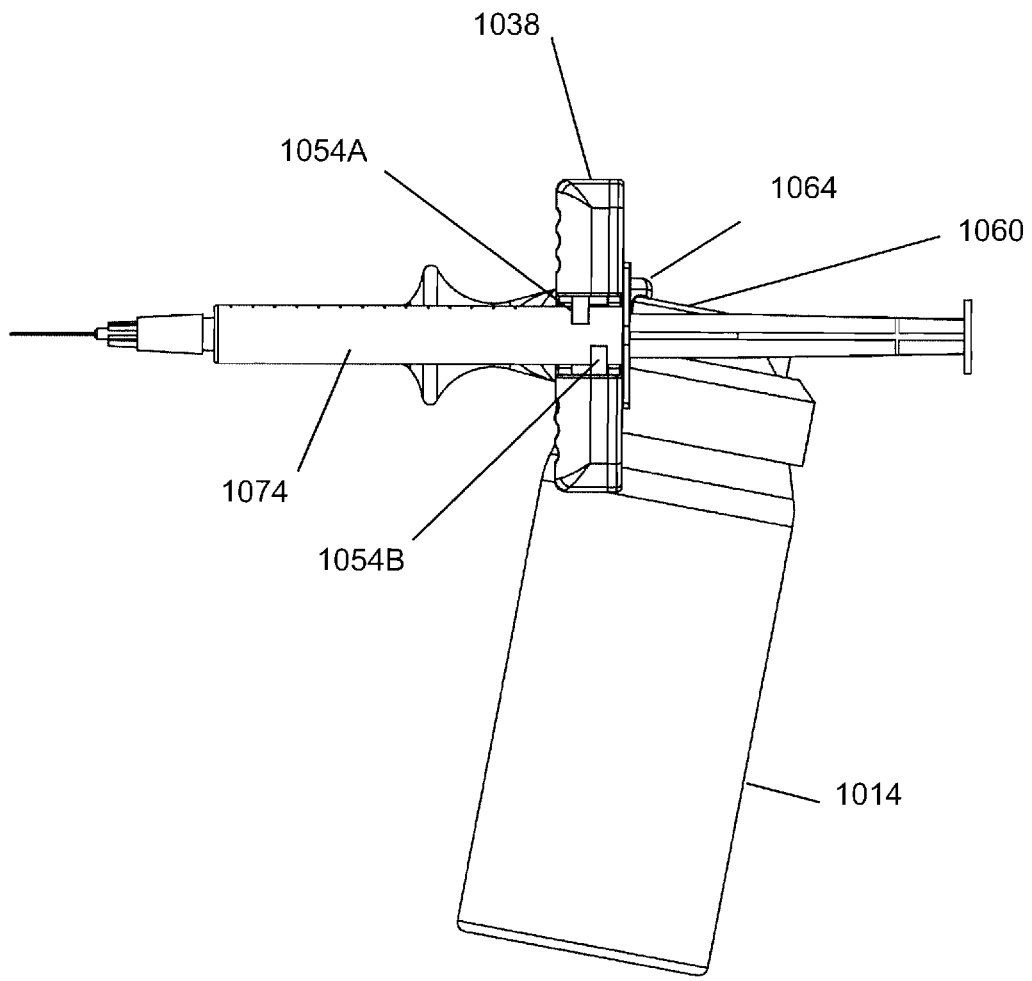
FIG. 26E is a left, side view of the canister with syringe holding nozzle, with a syringe attached thereto, shown in FIG. 26C.
Figure 26F:
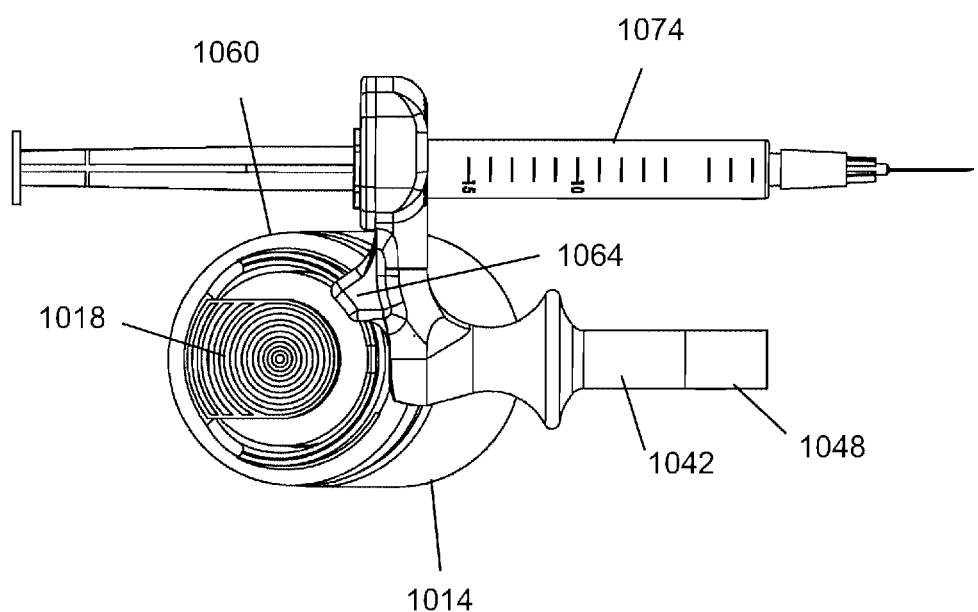
FIG. 26F is a top view of the canister with syringe holding nozzle, with a syringe attached thereto, shown in FIG. 26C.
Figure 26G:
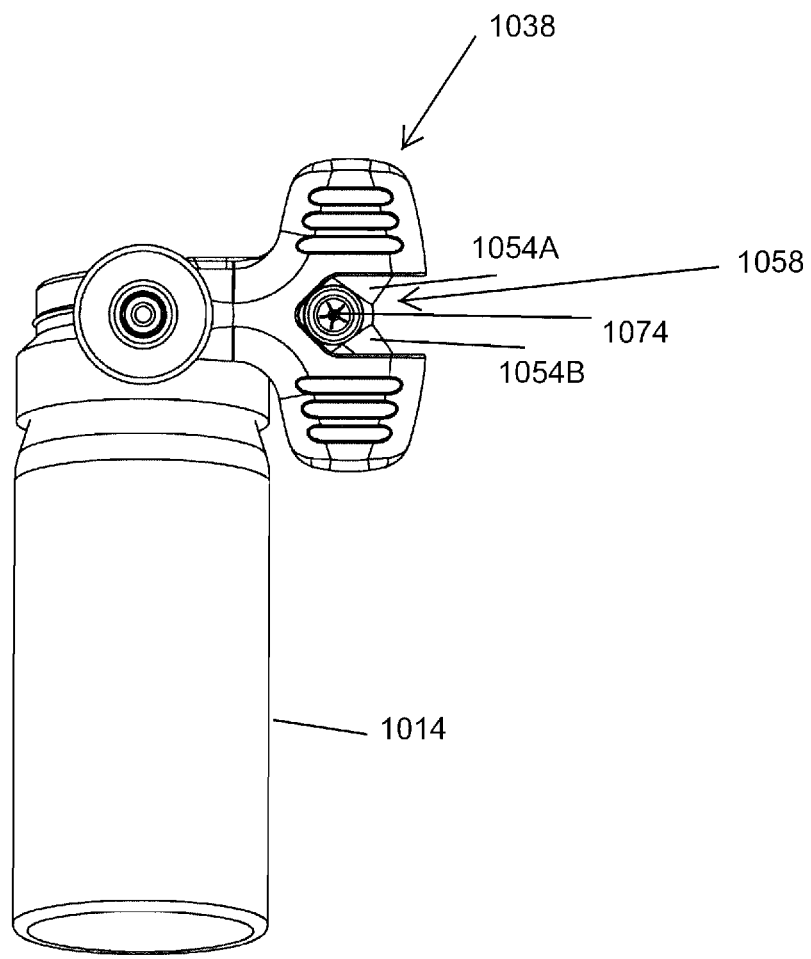
FIG. 26G is a front view of the canister with syringe holding nozzle, with a syringe attached thereto, shown in FIG. 26C.
Figure 26H:
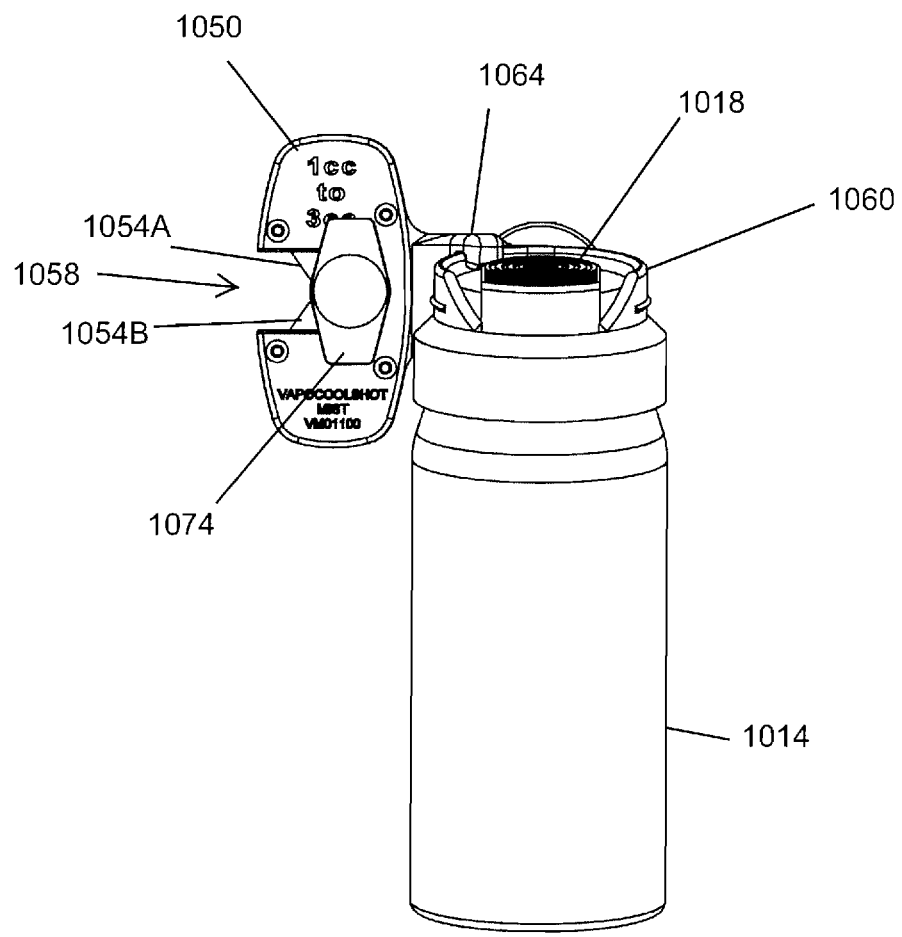
FIG. 26H is a rear view of the canister with syringe holding nozzle, with a syringe attached thereto, shown in FIG. 26C.
Figure 27:
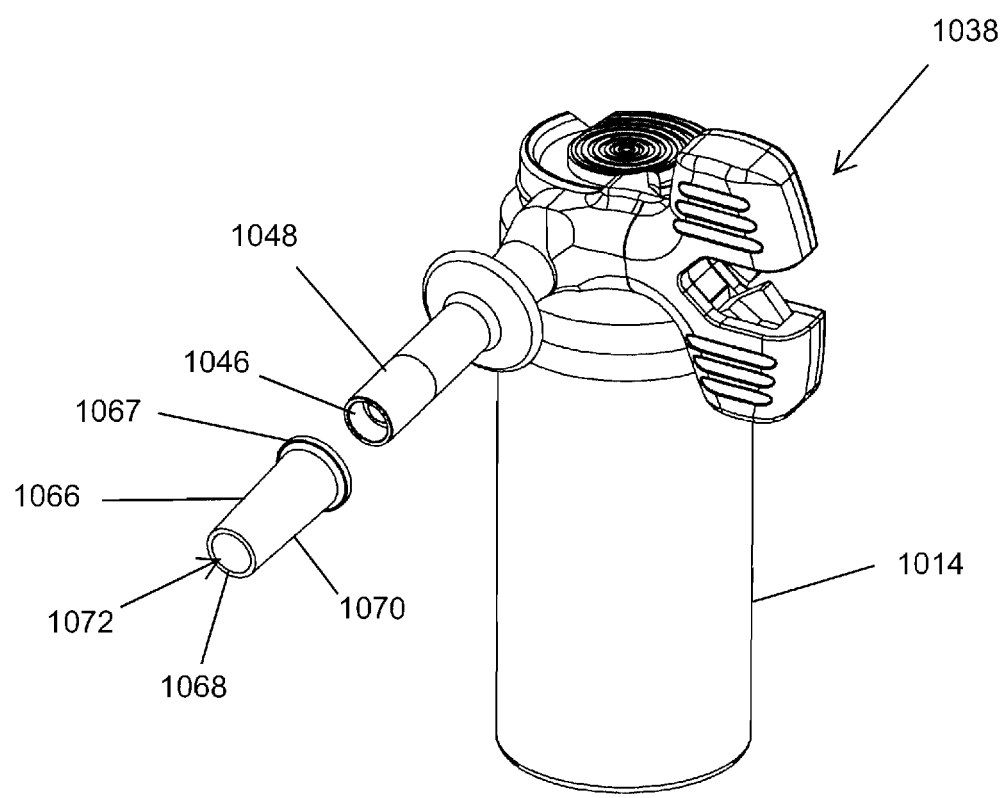
FIG. 27 illustrates a cap for attaching to the tip of the syringe holding nozzle.
Figure 28:
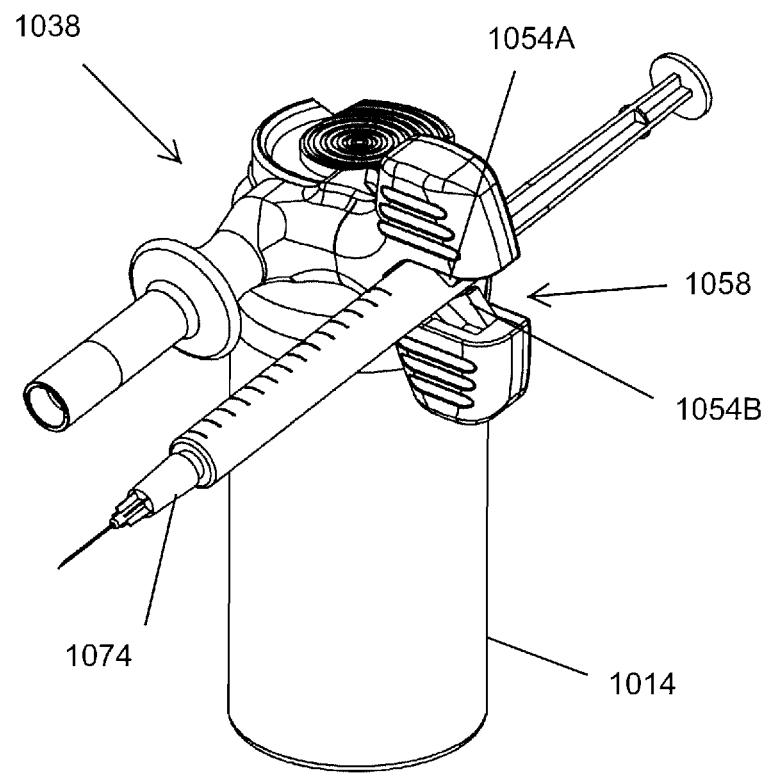
FIG. 28 is a top left front perspective view of the canister with syringe holding nozzle, with a syringe attached thereto, shown in FIG. 26C.

Referring to FIGS. 25-26H, the syringe holding nozzle 1038 is shown secured to canister 1014. In this manner, a user can dispense any medical agent, i.e. gaseous (vapor) anesthetizing composition, stored within the canister 1014. As illustrated in FIG. 26A, canister 1014 comprises a ridge or lip 1060. A canister engaging member 1062, illustrated herein as a hooked portion 1064 extending from the clamp body 1040 secures to the ridge or lip 1060, thus securing the syringe holding nozzle 1038 to the canister 1014, see FIGS. 26A-26H. when secured, the canister spout 1020 is placed within the syringe holding nozzle 1038, preferably within spout holding portion 1037, thus allowing fluid, i.e. medical agent, to dispense through a nozzle 1042, a nozzle tube 1044, a nozzle tip 1046, and a nozzle shroud 1048 and disperse out to the target area. A cap 1066 may be attached to the nozzle tip 1046 and/or the nozzle shroud 1048, see FIG. 27. The cap 1066 contains a first open end 1068, a second open end 1067, and a body 1070 having an inner lumen 1072. FIG. 28 illustrates a syringe 1074 engaged with the syringe holding nozzle 1038. As shown, the syringe barrel 1076 is inserted within the clamp body cut out section 1058, secured in place between the retracted clamps, 1054A and 1054B.

Figures 29, 30:
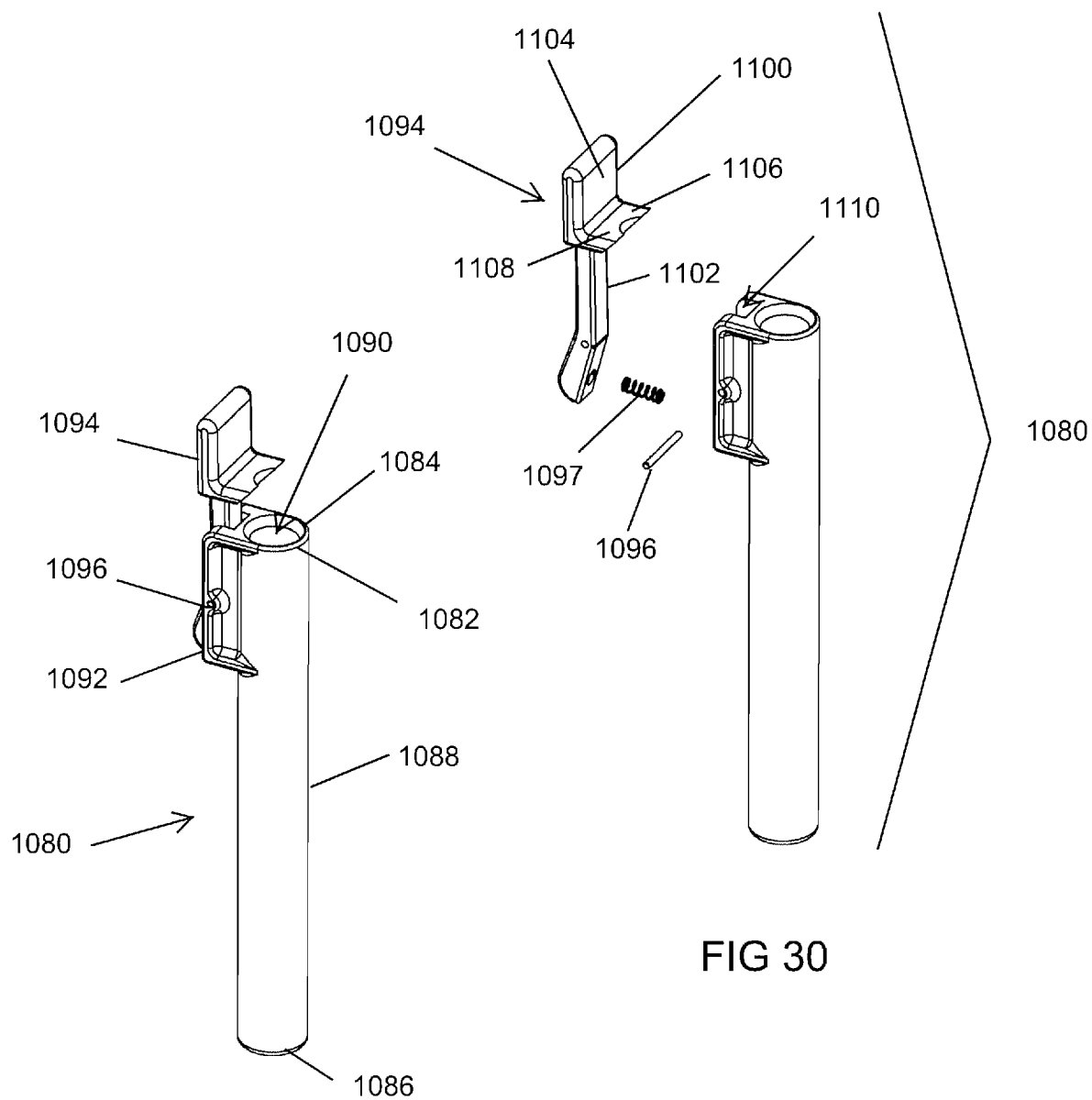
FIG. 29 is a perspective view of a syringe installation post.
FIG. 30 is an exploded view of the syringe installation post.

FIGS. 29 and 30 illustrate an embodiment of an installation post 1080. The installation post 1080 is configured to receive and hold one or more components or medical devices, such as a syringe 1074, which could be used in a medical procedure. The installation post 1080 comprises a first open end 1082 having an opening 1084, a second closed end 1086, and a main body 1088 therebetween. The main body 1088 has an interior 1090 sized and shaped to receive and hold the one or more components or medical devices. The first end 1082 may comprises a bracket 1092 which secures a latch 1094 thereto with a securing member, illustrated herein as a pin 1096. A spring 1097 allows the latch 1094 to move in a direction towards or away from the main body 1088. The latch 1094 comprises an upper portion 1100 and a lower portion 1102. The upper portion 1100 comprises a first surface 1104 and a second surface 1106 which extends out from the first surface 1104, thus forming a shoulder or ledge 1108. The bracket 1092 comprises a catch 1110, illustrated herein as a generally u-shaped cut out sized and shaped to receive and hold at least a portion of the lower portion 1102. The catch allows the latch to 1094 to move in a linear direction, but prevents side to side movement.

Figure 31A:
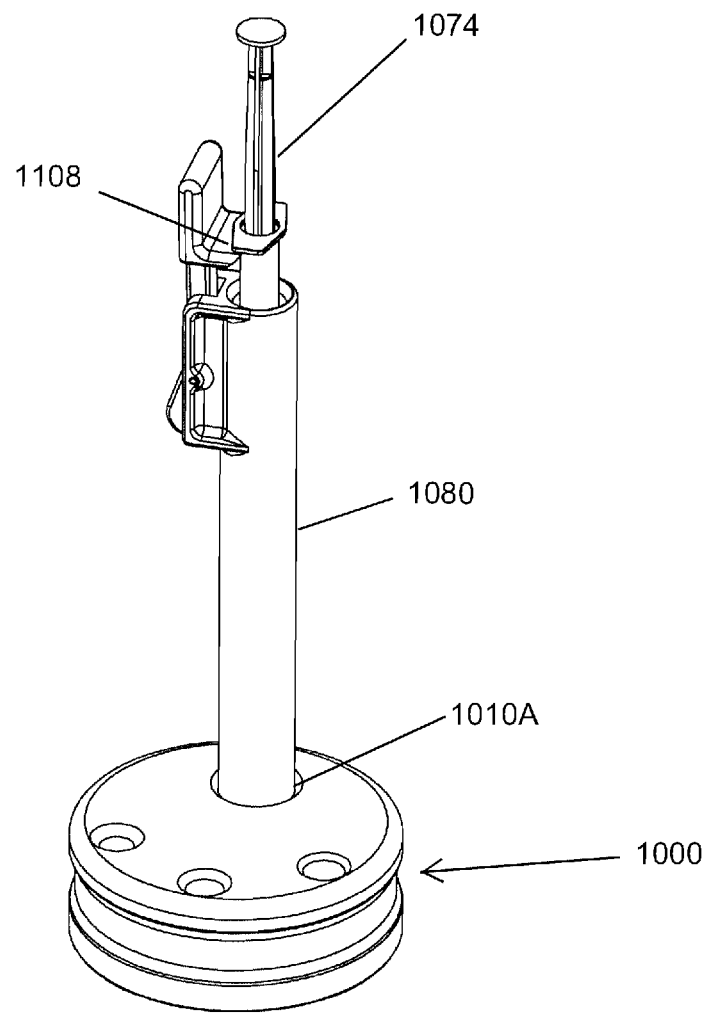
FIG. 31A illustrates the accessory holder unit illustrated in FIG. 17 with the syringe installation post inserted therein.
Figure 31B:
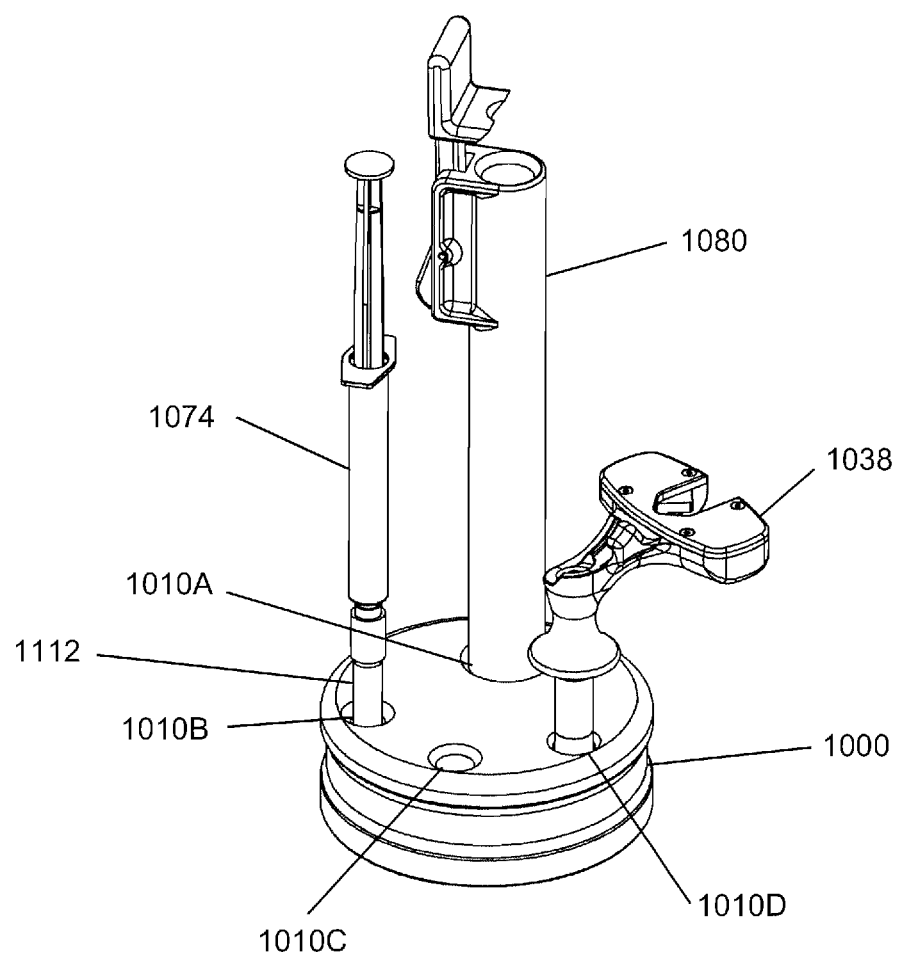
FIG. 31B illustrates the accessory holder unit illustrated in FIG. 17 with the syringe installation post, syringe, and syringe holding nozzle inserted therein.

Referring to FIG. 31A, the accessory holder 1000 is shown holding the installation post 1080 within opening 1010A. The installation post 1080 is also shown having a syringe 1074 inserted therein and resting on shoulder or ledge 1108. FIG. 31B illustrates the accessory holder 1000 with the installation post 1080 placed within opening 1010A, the syringe 1074 with a safety cap 1112 placed within opening 1010B, and syringe holding nozzle 1038 to be placed within opening 1010C.

All patents and publications mentioned in this specification are indicative of the levels of those skilled in the art to which the invention pertains.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A medical procedure accessory holding unit comprising:
   a support panel having two opposing side walls, a front wall, and an opposing back wall; and
   one or more medical device storage modules configured to store a component or instrument used in a medical procedure, wherein one of said medical device storage modules includes a syringe attachment module, said syringe attachment module being configured to allow a user to safely load a syringe and attach said syringe to a dispensing device, said syringe attachment module comprises a syringe attachment block and a syringe attachment block safety cover, the syringe attachment block including a syringe receiving area having a cut out region sized to accept a syringe body.

2. The medical procedure accessory holding unit according to claim 1, wherein said storage modules include four (4) medical device storage modules.

3. The medical procedure accessory holding unit according to claim 2, wherein one of said four (4) medical device storage modules includes a syringe disposal device module.

4. The medical procedure accessory holding unit according to claim 2, wherein one of said four (4) medical device storage modules includes a dispensing tool module.

5. The medical procedure accessory holding unit according to claim 2, wherein one of said four (4) medical device storage modules includes a canister module.

6. The medical procedure accessory holding unit according to claim 3, wherein said syringe disposal device module comprises a main body having an opening sized and shaped to receive and hold a syringe disposal device, said syringe disposal device module main body comprising an internal portion having a conjugate shape with respect to an outer shape of said syringe disposal device.

7. The medical procedure accessory holding unit according to claim 4, wherein said dispensing tool module comprises a dispensing tool module receiving body configured to receive and hold a dispensing tool.

8. The medical procedure accessory holding unit according to claim 7, wherein said dispensing tool module receiving body extends upwardly from a surface and comprises a first end, a second end, a closed end, and a shoulder.

9. The medical procedure accessory holding unit according to claim 5, wherein said canister module comprises a raised platform having one or more openings and corresponding internal compartments sized and shaped to received and store therein a canister(s) containing a medical agent to be used in a medical procedure.

10. The medical procedure accessory holding unit according to claim 1, wherein said syringe attachment block safety cover is configured to move in two directions, a first of said two directions providing a loading position for placing a syringe into the syringe attachment block and removing the syringe from the syringe attachment block, and a second of said two directions for covering a portion of the syringe and securing the dispensing device to the syringe.

11. The medical procedure accessory holding unit according to claim 5, further including at least one canister comprising one or more medical agents.

12. The medical procedure accessory holding unit according to claim 11, wherein said one or more medical agents is a gaseous anesthetizing composition.

\* \* \* \* \*